(12) United States Patent
Statham

(10) Patent No.: US 7,595,489 B2
(45) Date of Patent: Sep. 29, 2009

(54) METHOD AND APPARATUS FOR MATERIAL IDENTIFICATION

(75) Inventor: Peter John Statham, High Wycombe (GB)

(73) Assignee: Oxford Instruments Analytical Limited, Oxford (GB)

( * ) Notice: Subject to any disclaimer, the term of this patent is extended or adjusted under 35 U.S.C. 154(b) by 309 days.

(21) Appl. No.: 11/427,284

(22) Filed: Jun. 28, 2006

(65) Prior Publication Data

US 2006/0291619 A1    Dec. 28, 2006

(51) Int. Cl.
*G01N 23/201* (2006.01)
*G01T 1/36* (2006.01)

(52) U.S. Cl. .............. 250/310; 250/307; 250/311; 378/45; 378/46; 378/53; 702/40; 702/134; 702/137; 702/181; 702/189

(58) Field of Classification Search ............ 250/306, 250/307, 309–311, 360.09; 378/45, 46, 53, 378/56; 702/40, 134, 137, 173, 180, 181, 702/183, 189
See application file for complete search history.

(56) References Cited

U.S. PATENT DOCUMENTS

| | | | | |
|---|---|---|---|---|
| 4,260,885 A | * | 4/1981 | Albert | 378/45 |
| 5,299,138 A | * | 3/1994 | Fiori et al. | 702/22 |
| 6,118,850 A | * | 9/2000 | Mayo et al. | 378/83 |
| 6,140,643 A | * | 10/2000 | Brown et al. | 250/307 |
| 6,675,106 B1 | * | 1/2004 | Keenan et al. | 702/28 |
| 6,924,484 B1 | * | 8/2005 | Wang et al. | 250/310 |
| 6,996,492 B1 | | 2/2006 | Testoni | |
| 7,016,462 B1 | * | 3/2006 | Keville et al. | 378/47 |
| 7,132,652 B1 | * | 11/2006 | Testoni | 250/310 |
| 7,166,838 B1 | * | 1/2007 | Janik | 250/310 |
| 2002/0097834 A1 | * | 7/2002 | Satoh | 378/46 |
| 2004/0099805 A1 | * | 5/2004 | Ochiai et al. | 250/311 |
| 2006/0049349 A1 | * | 3/2006 | Shemesh | 250/310 |
| 2006/0291619 A1 | * | 12/2006 | Statham | 378/45 |

FOREIGN PATENT DOCUMENTS

JP    63108253    5/1988

OTHER PUBLICATIONS

Gauvin, Raynald et al., "On the Simulation of True EDS X-Ray Spectra", Microscp. Microanal., 2002, pp. 430-431, vol. 8, Suppl. 2, Microscopy Society of America.
Duncumb, Peter et al., "Improved X-ray Spectrum Simulation for Electron Microprobe Analysis", Microsc. Micronanal., Feb. 20, 2001, pp. 341-355, vol. 7, Microscopy Society of America.

(Continued)

*Primary Examiner*—Bernard E Souw
(74) *Attorney, Agent, or Firm*—Vern Maine & Associates

(57) ABSTRACT

A method of identifying a material using an x-ray emission characteristic is provided. X-ray data representing a monitored x-ray emission characteristic is obtained from a specimen in response to an incident energy beam. A dataset is also obtained, this comprising composition data of a plurality of materials. The material of the specimen is contained within the dataset. Predicted x-ray data are calculated for each of the materials in the dataset using the composition data. The obtained and the predicted x-ray data are compared and the likely identity of the material of the specimen is determined, based upon the comparison.

32 Claims, 3 Drawing Sheets

OTHER PUBLICATIONS

Duncumb, Peter et al., "Benefits of X-ray spectrum simulation at low energies", Microchimica Acta, May 2002, pp. 249-258, vol. 138, No. 3-4, Springer Wien.

Pouchou, Jean-Louis et al., "Quantitative Analysis of Homogeneous or Stratified Microvolumes Applying the Model "Pap"", Electron Probe Quantitation, 1991, pp. 31- 75, Plenum Press, NY.

Mantler, "VXRF: A Software Package for Teaching (and Learning) XRF", Advances in X-ray Analysis, 2000, pp. 429-434, vol. 43, JCPDS—International Centre for Diffraction Data.

Ao, Q. et al., "Development of the Specific Purpose Monte Carlo Code CEARXRF for the Design and Use of in Vivo X-ray Fluorescence Analysis Systems for Lead in Bone", App. Radiat. Isot., 1997, pp. 1403-1412, vol. 48, No. 10-12, Elsevier Science Ltd., Great Britian.

Statham, Peter J., "A Check Total for Validating Standardless and Normalised EDX Analysis At Low KV", Mikrochimica Acta, 2004, pp. 229-235, vol. 145.

Statham, Peter J., "Deconvolution and Background Subtraction by Least-Squares Fitting with Prefiltering of Spectra", Analytical Chemistry, Dec. 1977, pp. 2149-2154, vol. 49, No. 14.

Fluck, Ekkehard, "Inorganic Crystal Structure Database (ICSD) and Standardized Data and Crystal Chemical Characterization of Inorganic Structure Types (TYPIX)—Two Tools for Inorganic Chemists and Crystallographers", J. Res. Natl. Inst. Stand. Technol., May-Jun. 1996, pp. 217-220, vol. 101, No. 3.

EP Search Report dated Oct. 26, 2006 of U.S. Appl. No. 06/252,989, filed Jun. 9, 2006.

Newbury, Dale E., "Standardless Quantitative Electron-Excited X-ray Microanalysis by Energy-Dispersive Spectrometry: What is its Proper Role?", Microscopy and Microanalysis, 1999, pp. 585-597, vol. 4.

Duncumb, Peter et al.,"Improved X-ray Spectrum Simulation for Electron Microprobe Analysis", Microanalysis, 2001, pp. 1-15, vol. 7.

Mandal, A.C. et al., "Bremsstrahlung Excited Standardless EDXRF Analysis", Nuclear Instruments and Methods in Physics Research, 2004, pp. 104-112, vol. B 217, Elsevier B.V.

Duncumb Peter et al., "Benefits of X-Ray Spectrum Simulation at Low Energies", Mikrochimica Acta, 2002, pp. 249-258, vol. 138.

* cited by examiner

METHOD AND APPARATUS FOR MATERIAL IDENTIFICATION

FIELD OF THE INVENTION

The present invention relates to a method for identifying a material, together with corresponding apparatus and software for performing the method.

BACKGROUND OF THE INVENTION

In forensic analysis, semiconductor defect review, gunshot residue analysis and general materials analysis of alloys, ceramics, glasses, minerals, polymers and powders, the identity of a fragment of material can often be determined by collecting and analysing an x-ray energy spectrum. The x-rays can be excited from the fragment for example by a beam of x-rays (x-ray fluorescence, XRF) or electrons (electron probe microanalysis, EPMA) or protons (proton induced x-ray emission, PIXE). X-rays are often detected by an energy dispersive x-ray detector (EDX) which is typically a lithium drifted Si, Si(Li), detector or a silicon drift detector, SDD. For example, in U.S. Pat. No. 6,326,619, energy-dispersive x-ray (EDX) analysis is used in a scanning electron microscope (SEM) to find a list of major elements present in the sample and this list is used to filter and select only those entries in the crystallographic database that have at least these elements. This narrows down the number of candidates that need to have their crystallography compared by EBSD pattern analysis.

In U.S. Pat. No. 6,835,931 EDX analysis is used to provide a "chemical filter". The amounts of each element found by analysis of the EDX spectrum are compared with upper and lower limits for each of the phases in a list of phases that may be present in the region of interest and the crystallographic information obtained by EBSD then compared with that stored with the list of phases to find out which crystallographic phase is present.

In both these methods, some measure of the amount of each element present in the sample is required to decide which entries in a database are appropriate, thus providing a filter for those entries. An alternative approach is to use "spectral fingerprinting" to find out what material has a composition closest to the sample being analysed. Some examples of this approach include JP-A-108253/1988, US2004/0099805, U.S. Pat. No. 6,519,315 and U.S. Pat. No. 6,140,643.

When an x-ray spectrum is measured by for example EDX, sharp peaks appear in the spectrum for each chemical element in the sample corresponding to the characteristic line emissions for that element and a broad background appears due to continuous physical effects within the sample. To obtain the amounts of each element present, mathematical processing of the digitised energy spectrum is required to correct for the continuous background and resolve any overlapping peaks from different elements. Errors in background subtraction, slight miscalibration of the spectrometer or incorrect characterisation of peak shape can result in inaccurate estimates of peak areas. Furthermore, to convert the areas into mass concentration for elements requires x-ray correction procedures that may introduce additional sources of inaccuracy. Even if two chemical elements are present in the sample at the same mass concentration level, the efficiency of x-ray production may sometimes differ so that the characteristic peaks have areas that may be different by orders of magnitude. Some characteristic radiation at low energy may be heavily absorbed on exit from the sample and by materials within the detector entrance window so that the peak may not be detectable in the spectrum.

The source of excitation, whether electron beam or x-ray beam, defines the maximum energy of the emitted radiation from the sample and if the maximum energy in the source is too low, then some characteristic lines at higher energy may not be excited. If the total counts recorded in the x-ray spectrum is too low, then the statistical precision in background subtraction may be insufficient to reliably detect very low intensity characteristic peaks. If the source of excitation scatters off the sample and strikes material other than the sample being analysed, including material within the detector entrance window, then spurious peaks appear in the spectrum. These spurious peaks may be misidentified as elements from within the sample. Even if these peaks are small, the apparent mass concentration for the misidentified element may be large after the peak area is corrected for excitation efficiency and any anticipated effects of absorption.

As a consequence, x-ray spectral analysis may sometimes fail to detect certain elements present in the sample, may detect elements which are not present in the sample (false positives) and may give concentration estimates which are inaccurate. When elemental compositional analysis is used as a filter to select candidates from a large database, tolerance limits can be relaxed to allow for errors in concentration and a subset of detectable elements can be used to avoid the problems of missing elements. However, the occurrence of false positives from spectral analysis can exclude the correct candidate within the database. Even if there are no false positives, relaxing the tolerance on upper and lower concentration limits may allow far too many candidates to be allowed through so that the filter is not effective in restricting the choice of likely material for the sample.

"Spectrum matching", provides a means of overcoming some of the difficulties of the filtering. In this approach, some metric is evaluated for the unknown and a reference spectrum from a known material. By evaluating the metric for a large number of reference spectra of known materials and ranking the results in order of increasing value, candidate materials are provided in order of similarity to the unknown. Spurious peaks that would cause a filtering approach to fail completely will usually only provide a small change to the metric so even if the reference spectrum for the correct material does not give the best match, the metric will usually put it in the top few best matches. Thus selection of the correct material by other techniques is made easier. This "spectrum matching", like fuzzy logic approaches, avoids the sharp exclusion properties of a filter while offering some tolerance of errors and some assistance in choosing between similar candidate materials.

The problem with the spectrum matching approach is that reference spectra need to be acquired for all candidate materials and structures under similar conditions to that used to acquire the spectrum from the unknown sample. This limits the practical number of materials that can be identified and the conditions that can be used for analysis. Furthermore, the spectrometer used to measure spectra from the reference materials usually has to have similar resolution and efficiency to the spectrometer used for measuring the unknown sample.

SUMMARY OF THE INVENTION

In accordance with a first aspect of the present invention, we provide a method of identifying a material using an x-ray emission characteristic, the method comprising:

a) obtaining x-ray data representing a monitored x-ray emission characteristic of a specimen in response to an incident energy beam;

b) obtaining a pre-existing dataset comprising composition data of a plurality of materials and wherein the material of the specimen is contained within the dataset;

c) calculating predicted x-ray data for each of the materials in the dataset using the composition data;

d) comparing the obtained and the predicted x-ray data; and e) determining the likely identity of the material of the specimen, based upon the comparison.

The invention therefore allows for the calculation of the predicted X-ray data from data describing such materials in the dataset obtained in step (b). This is achievable with sufficient accuracy so as to allow identification of the material in question, or at least a number of likely candidate materials. Typically the dataset comprises at least composition data for a very large number of materials. Although the size of the required dataset depends upon the application, the dataset is in each case sufficiently comprehensive so as to guarantee that the specimen material is present within it. Thus the invention concerns identifying a set of one or more candidate materials from the dataset, one of which will be the material of the specimen. It is therefore no longer necessary to perform measurements in order to obtain x-ray emission characteristics from actual specimens of every candidate material in the database. As a result, spectral matching can be used to identify materials even when there is no reference material available or the number of candidate materials is so large that direct measurement of spectra from all candidates would be impractical. In addition, the quality of the data for the comparison is no longer dependent upon the particular conditions under which an actual physical experiment was made in order to obtain the data for the comparison. Typically the dataset is extremely comprehensive and may, for example, include at least materials composition data for large material groups such as all known metals or all known inorganic crystalline solids.

Typically the predicted x-ray data in step (c) are similar to the data which would have been obtained if the incident radiation beam were incident upon a specimen containing the corresponding material as described by the materials data in the database. The method used to perform the calculation of the predicted x-ray data in step (c) is dependent upon the particular x-ray emission characteristic obtaining within step (a). Various models can be used to perform step (c). The model for example may be based upon ZAF theory where the model calculates x-ray intensities based upon an x-ray generation contribution, an absorption contribution and a fluorescence contribution, symbolized by the symbols Z (x-ray generation), A (absorption), and F (florescence), from which the model's name is derived. Preferably the model also calculates the x-ray background continuum. The model may then calculate the ratio of peak intensity to total background intensity. Recently it has become possible to perform accurate predictions using Monte Carlo modelling techniques ((e.g. R. Gauvin and L. Lifshin (2002), "On the Simulation of True EDS X-Ray Spectra", Microscopy & Microanalysis, Vol. 8, Supp. 2, pp. 430-431, 2002.). A Monte Carlo model can therefore be used and is particularly beneficial in the calculation of predicted x-ray data for materials where the structure of the sample material affects the x-ray output.

In order for the method to be of use in practical situations, it is extremely important that the accuracy of the predicted x-ray data is sufficiently high. The method therefore preferably further comprises, prior to step (a), validating the accuracy of the calculation method for step (c) by comparing test calculations with experimentally obtained test x-ray data. The method of calculating in step (c), such as a model, may then be calibrated or adjusted in accordance with the test data results in order to give improved accuracy when the x-ray output is calculated for an arbitrary material. Whilst it is important to ensure the accuracy of such calculations, in doing so great benefit is achieved in that it is then always possible to synthesise x-ray data even when it is not possible practically to obtain useful experimental data from a material standard as would have been required in the prior art. Therefore the present method provides the ability to identify materials even when prior art methods using standards would be unable to do so.

In many cases the x-ray emission characteristic is an x-ray spectrum and various different spectra types may be used depending upon the method in which the x-ray data is obtained in step (a).

The calculating step may be based upon data describing the analytical conditions under which the data in step (a) were obtained and/or based upon data describing the x-ray apparatus used in obtaining the data.

In some instances, such as when an electron or ion beam is used, the sample may become charged prior to or during the step of obtaining the data from the specimen. This may accordingly influence the x-ray emission characteristic in question and therefore preferably in this case, the method further comprises taking such charging into account by calculating the effect of such charging in step (c).

Since predicted data are calculated for a number of materials having corresponding data within the dataset, the result of their comparison is preferably some measure of correlation between the predicted and obtained data. Typically this measure of correlation takes the form of a matching parameter. It will be appreciated that the comparison step (d) may use some or all of the data obtained in step (a) and that calculated in step (c). In some cases it is beneficial to use only part of such data and therefore when a spectrum is represented by the data, a matching parameter in step (d) may be calculated only in regions within the spectrum containing peaks and is independent of the peak intensity in such regions. In other cases, such as for low energy measurements, the matching parameter in step (d) may be calculated based upon the bremsstrahlung background of the spectrum.

Although various detectors may be used in obtaining the x-ray emission characteristic in step (a), when such a detector comprises a multichannel detector with associated data, the matching parameter in step (d) may be calculated based upon the normalised cross-correlation coefficient for all channels of the obtained x-ray data. Alternatively, as in cases mentioned above, the matching parameter in step (d) may be calculated upon only the channels near or containing peaks in the spectrum which are significant peaks with respect to the statistical noise.

The matching parameter in step (d) may also be calculated based upon a weighting factor for different channels or indeed combinations of matching parameter calculations such as by using a weighted sum or a product of the matching parameters calculated as described above.

Once the matching parameter has been calculated using data for each of the materials in question, this may be compared against a predetermined threshold so as to select a sub-set of candidate materials. The matching parameter may be used to rank materials likely to be a material of the specimen.

The matching parameter may therefore be used to select the top N likely materials from the dataset, and a second matching parameter may be used to further rank the selected calculated materials.

The method also contemplates the use of a pre-selection based upon knowledge of the specimen itself. If for example the material of the specimen is known to be metallic then step (c) can be performed upon a pre-selected dataset only containing such materials, namely, only metallic materials.

In some cases, the specimen may comprise a small quantity of the material in question, in which case the x-ray emission characteristic may include a component or influence from the substrate or holder of the specimen material. In addition, the specimen may be formed from a number of materials, such as a multilayer specimen. Preferably therefore the dataset further comprises structure data wherein the identified material includes an associated structure of the specimen. This includes the provision of an additional "structure" dataset. Such structure data may take various forms, including the dimensions or one or more components of the associated structure. This is in addition to the remainder of the material data which contains at least the composition of the material.

Preferably each of the materials is identified in the dataset using an associated identifying code, which may also be a code related to the structure.

In cases where there are multiple materials within the specimen, or a small specimen such that artefacts are present from the substrate, the method may further comprise obtaining the x-ray characteristic data under two or more different incident beam conditions. In this case, when the characteristic data in step (a) represents data obtained from the specimen under two or more different incident beam conditions, the predicted data in step (c) is calculated for each different condition, and the determination in step (e) is based upon the different incident beam conditions. Such conditions may include different incident beam energies. Of course, such a method may also be used in order to distinguish between specimens without such a structure, in the event that for example it is difficult to identify the specimen material.

Although step (a) is related to obtaining the x-ray data, the method may further comprise, (prior to step (a)), the following steps of:
  i) Positioning the specimen within an x-ray emission detecting apparatus comprising an x-ray detector;
  ii) Causing the energy beam to be incident upon the specimen so as to cause the specimen to emit x-rays; and
  iii) Detecting the x-rays with the detector.
  The incident beam may take a number of forms, including an electron beam, x-ray beam or ion beam.

The method is preferably performed by computer software and therefore the invention includes a computer program comprising computer program code means adapted to perform the method when the computer program is executed upon a computer. The invention also extends to a computer readable medium comprising such a computer program.

In accordance with a second aspect of the present invention, we provide an x-ray system for material identification comprising:
  an x-ray analysis apparatus in which is placed in use a specimen containing a material to be identified, the apparatus having a beam generation device, a specimen holder and an x-ray detector; and,
  a controller adapted in use in perform the method in accordance with the first aspect of the invention.

As will be appreciated, the x-ray analysis apparatus may take a number of forms, including an electron microscope or an x-ray fluorescence analysis instrument. When an x-ray beam is used in such an instrument, preferably the x-ray beam is collimated or focussed by an x-ray optic to a small region where it is incident upon the specimen. The detector for use in such a system may take a number forms including a solid state detector or a gaseous proportional detector.

In summary, the invention builds on the advantages of a spectrum matching approach while avoiding the need to measure spectra from a large collection of reference materials. Variations in excitation conditions and in the resolution and efficiency of the x-ray detection system can be accommodated with no need to acquire data from reference materials. The invention provides the ability to take the composition of the material, the analytical conditions and the parameters of the x-ray detection system and make an accurate prediction of the spectrum that would be generated. While it is always possible to predict a spectrum given information on material composition and structure, it is not always possible to deduce the composition and structure from an experimental spectrum. Therefore a dataset of materials can be used to provide a method for identification of an unknown material, even though the composition of the material may be impossible to measure by conventional analytical techniques.

BRIEF DESCRIPTION OF THE DRAWINGS

Some examples of a method and apparatus according to the invention are now described with reference to the accompanying drawings in which.

DETAILED DESCRIPTION

Figure 1:
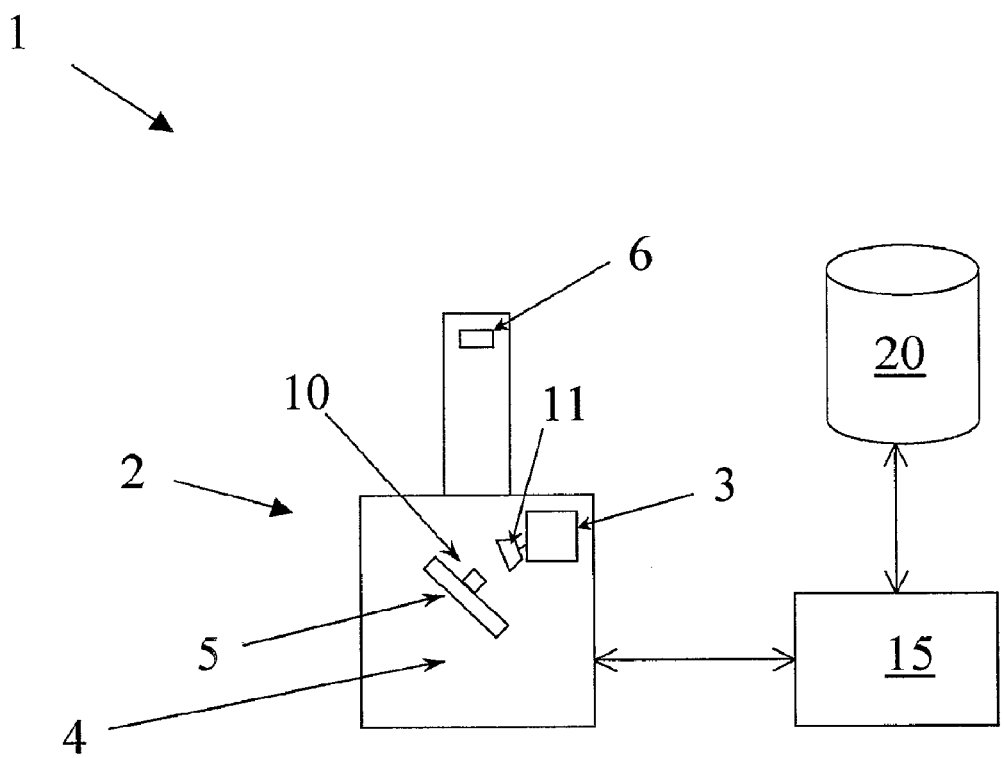
FIG. 1 shows an example system.

An overview of a system 1 for performing the invention is shown in FIG. 1. The system comprises a scanning electron microscope (SEM) 2 having an x-ray analysis system 3, this being an INCA Energy x-ray analysis system (manufactured by Oxford Instruments Analytical Limited). The SEM has a chamber 4 containing a specimen holder 5 which can be tilted. An incident beam of electrons is emitted by an electron gun 6, this being focused upon a specimen 10 held within the specimen holder. Characteristic x-rays that are emitted as a result of the electron beam are detected by a detector 11 forming part of the x-ray analysis system 3.

The system 1 includes a control computer 15 upon which software is executed to control the operation of the system 1. The computer 15 is in communication with a remote database 20 using an appropriate communications link such as the Internet. The database 20 retains a database of materials data for use by the SEM software. In an alternative example the database could be retained locally, such as on the computer hard disk.

Figure 2:
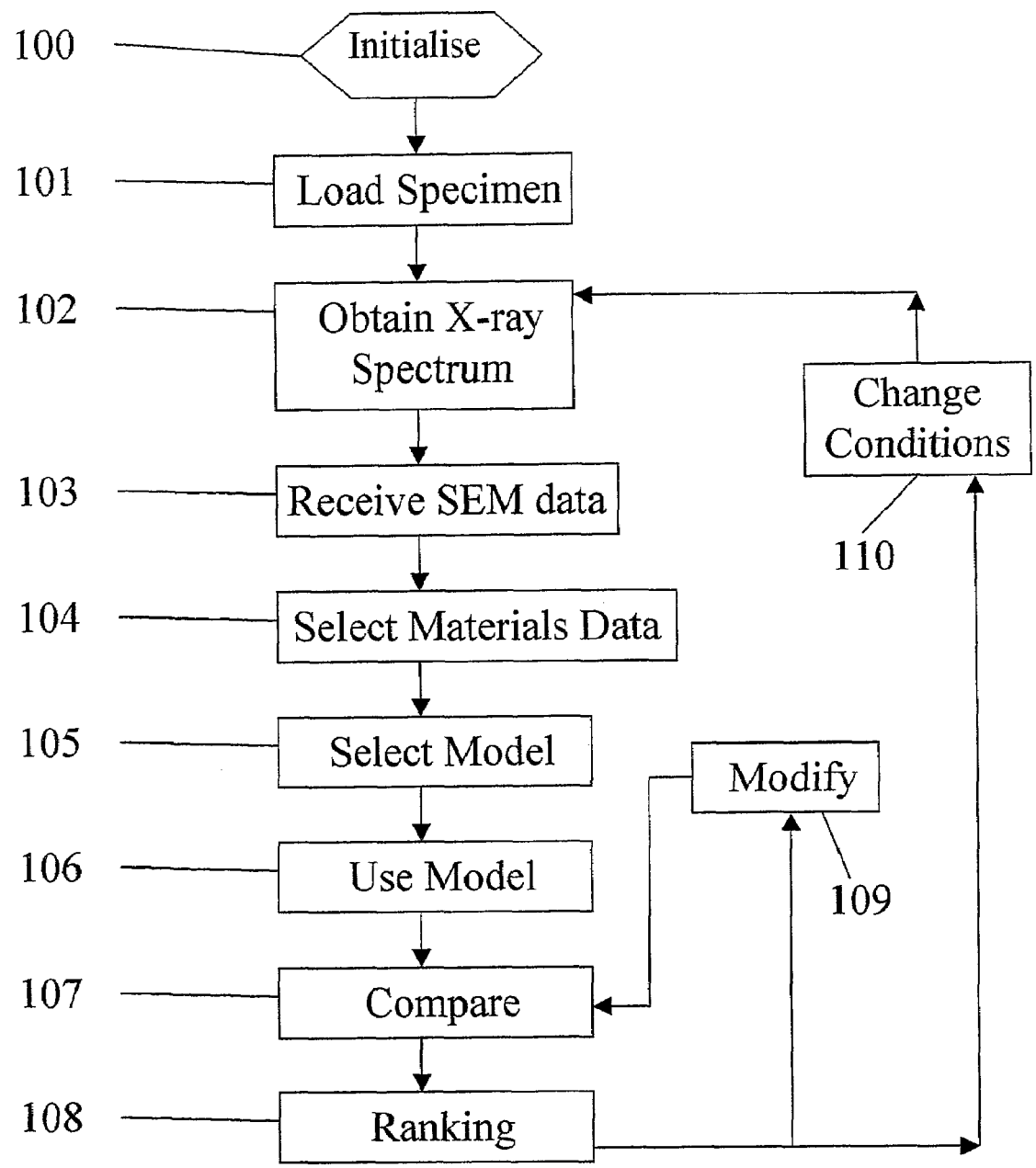
FIG. 2 is a flow diagram of an example method.

Referring now to FIG. 2, an example method of using the system of FIG. 1 is described.

At step 100 the system is initialized and the SEM chamber 4 is vented to received a specimen to be analysed. A specimen 10 whose materials and possibly structure it is desired to determine is loaded into the specimen holder 5 of the SEM 2 at step 101. The operator of the system may initially instruct the control computer software that the specimen is of a particular type, such as a metallic specimen.

At step 102, a monitoring step is performed in which the chamber 4 is pumped to vacuum and the electron gun 6 is operated (together with the specimen holder 5, electromagnetic lenses and so on), so as to focus an electron beam onto the specimen 10. The computer 15 operates the x-ray analysis system 3 such that x-rays emitted from the specimen as a result of the electron beam stimulation are detected by the detector 11 and converted into characteristic data in the form of an x-ray spectrum.

The control computer receives the spectrum data at step 103. In addition to the spectrum itself, the computer may also interrogate the SEM 2 for the analytical conditions under which the specimen was monitored such as the incident beam energy, beam current, sample tilt and orientation. The computer may interrogate the x-ray analysis system for the detector response function and may calculate from the spectrum itself the high energy limit that gives the landing energy of the incident beam that indicates charging when this is less than the incident beam energy.

At step 104, the computer 15 selects materials data which are descriptive of a set of possible specimen material types, from the database 20. Optionally, this is based upon any limitations upon the specimen type entered by the user, an example limitation being that the specimen material is an insulator. The selected materials data forms the dataset which may therefore comprise part of the database or all of it.

The materials dataset contains information including a unique identifier, compositional information and, in some cases, structural information. For example, the structural information is present in the case where the specimens have structures such as small dimensions or are multi-layered or have voids, in either case where there may be a contribution from the substrate upon which the specimen is mounted.

At step 105, a prediction model is selected in order to calculate the predicted x-ray spectrum data using the materials data. Such a model may be selected by the user, or selected automatically based upon the materials data obtained in step 104. A number of such models can be used depending upon the application in question. For electron beam excitation of a bulk sample an accurate theoretical model has been achieved ("Improved X-ray Spectrum Simulation for Electron Microprobe Analysis", Peter Duncumb, Ian R. Barkshire, Peter J. Statham, Microsc. Microanal. 7, 341-355, 2001.). This paper, together with the other papers mentioned herein are incorporated by reference thereto. The model can extended to deal with low beam voltages and overlayers ("Benefits of X-Ray spectrum simulation at low energies", P. Duncumb and P. J. Statham, Mikrochimica Acta, 138, 249-258, 2002) and can be combined with existing models to predict intensity for multilayers on substrates ("Quantitative analysis of homogeneous or stratified microvolumes applying the model "PAP".", Pouchou, J. L. & Pichoir, F. (1991) In: Electron Probe Quantitation, Heinrich, K. F. J. & Newbury, D. E. (eds), Plenum Press, New York, 31-75). For x-ray beam excitation, existing models are less accurate but generalised theoretical spectrum simulation software is available ("VXRF: A software-package for teaching and learning XRF", Mantler M., Adv. X-Ray Analysis, 43 (2000) 429-434) and more accurate models have been developed for specific application areas ("Development of the specific purpose Monte Carlo code CEARXRF for the design and use of in vivo X-ray fluorescence analysis systems for lead in bone", Ao Q, Lee SH, Gardner RP, Appl Radiat Isot. 1997 October-December; 48(10-12):1403-12).

A summary of a model suitable for implementing the present example is given in the Appendix. This refers to the disclosure of the paper "Improved x-ray spectrum simulation for electron microprobe analysis", mentioned earlier and the contents of which, particularly the "Theory" section of that paper (pages 345 to 351) are intended to be contained by reference within the disclosure of the present application.

Returning to the present method, having selected the model, at step 106 the materials data are entered into the model for each material (and possible structure) selected at step 104. The model generates predicted data, in the present case this taking the form of a predicted x-ray spectrum. The form of the predicted spectrum is that which would be expected to be detected by the system 1 if the material in question (described by the materials data) were in fact placed within the SEM 2 and analysed under the excitation conditions in question.

At step 107 the theoretical spectrum from each material is then compared to the monitored spectrum from the unknown specimen. A matching parameter in the form of a similarity measure is assigned to each giving the closeness of match.

The similarity measure (matching parameter) can be chosen to make the method tolerant of likely experimental problems or inaccuracies in the theoretical model. For example, if the specimen begins to charge negatively in an electron microscope, then the landing energy for incident electrons is reduced and the relative excitation of characteristic lines changes. In this situation, conventional x-ray analysis would give the incorrect result for elemental mass concentrations calculated from characteristic x-ray peak intensities. Furthermore, the spectrum is also different when the sample is charged or uncharged. The landing energy determines the highest energy for x-rays in the spectrum (the "Duanne Hunt Limit" or DHL). In the spectrum for energies below DHL, the characteristic peaks still identify the elements present in the specimen but their relative intensities are different from those from an uncharged specimen. If the similarity measure is only calculated in regions where there are peaks in the measured spectrum and in each region the measure is made independent of peak intensity, then the sum of all measures in such regions is independent of the effects of charging. Any differences in elemental content between specimen and reference material will still affect the similarity of spectra and ensure that the correct material is still high in the ranked list of candidates.

The matching parameter can alternatively be chosen to be sensitive to other properties of the spectrum such as the background. For example, in an electron microscope at low accelerating voltages, the incident beam may not be energetic enough to excite characteristic x-rays from every element in the periodic table. However, the bremsstrahlung background is influenced by all elements present in the material. A spectrum synthesis tool can estimate the expected ratio of the sum of all characteristic peaks to all the background in the spectrum and this can be used to verify consistency of element composition with the observed spectrum (see for example. "A check total for validating standardless and normalised edx analysis at low kV" P. J. Statham,. Mikrochimica Acta, 145, 229-235 (2004)). If the beam current is known, or the spectrum intensity is compared to that from a known sample, then the intensity of all the energy channels in the spectrum can be compared with that of the synthesised spectrum, since this varies with elemental content even in cases where few characteristic peaks are excited.

At step 108, a ranked list of the "best matches" is prepared based upon the result of the comparison. For example the predictions with the top 5 numerical values of the matching parameter can be presented. Alternatively, those with a value above a predetermined threshold can be presented to the user. This ranking is displayed to the user to show the most likely materials for the unknown sample. The displayed ranking may include the numerical value of the matching parameter.

The user can then use the ranking to fully identify the material of the specimen or at least identify the material as one of a number of likely candidates. In some cases it will be appreciated that a large number of likely materials may result and in this case a further comparison step can be performed at step 109. A different method of comparison may be chosen here, resulting in a different matching parameter. Those materials which fare best on the basis of both matching parameters can be ranked highly.

In situations where the unknown sample is not homogeneous, for example a film or particle on a substrate, possibly with overlayers, then the dataset comprising the database 20 of materials data may be extended to include the dimensions of candidate structures with the elemental composition of each material constituting the structure. Each structure type in the database is given an identity code. The theoretical calculation model is then used to synthesise the x-ray spectrum from each candidate structure in the dataset and compare it with the measured spectrum from the unknown sample in a similar manner to the method described above. The identity codes of the candidate structures are then prepared in a list ranked according to the closeness of match.

For such non-homogeneous samples, additional information may be obtained by acquiring more than one spectrum using different excitation energies. This is illustrated at step 110.

In this case, the theoretical calculation model is used to synthesise spectra from all the candidate structures at the different excitation energies. By comparing the measured spectrum from the unknown with synthesised spectra for all candidate structures, ranked lists of matches are obtained for each excitation energy. In general, the lower excitation energy will favour those parts of the structure close to the surface so when an ideal match is not obtained, it is still possible to find out what candidate structure best matches the unknown either on the surface or further below the surface.

Some specific examples of the use of the invention are now described.

EXAMPLE 1

Figure 3:
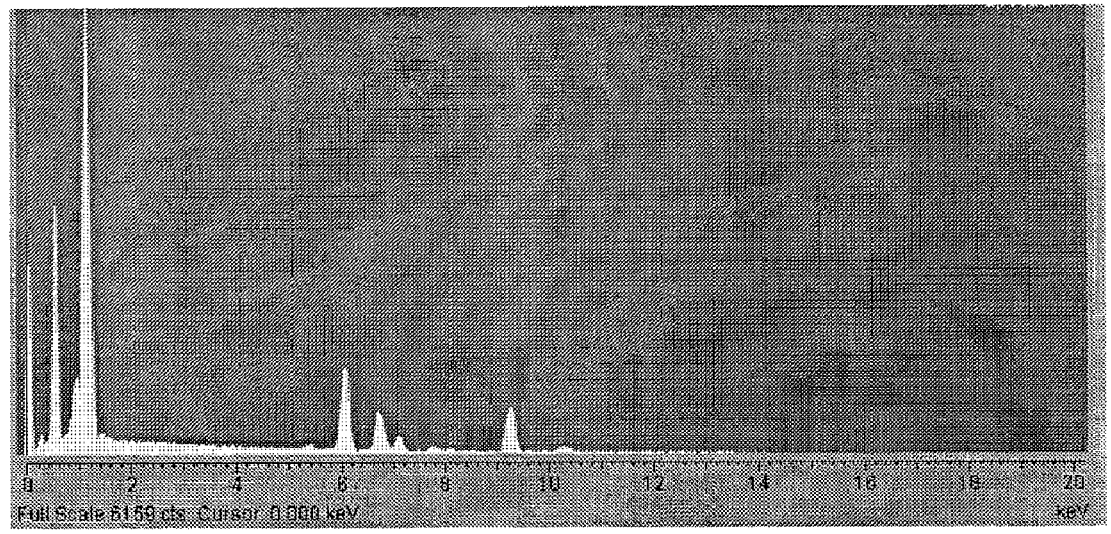
FIG. 3 is an x-ray energy spectrum using a Si(Li) detector according to a first example.

In this first example, a sample of $Gd_3Ga_5O_{12}$ with surface at approximately 70 degree surface tilt is placed in the electron microscope 2 using a 20 kV accelerating voltage and the spectrum is recorded using the Oxford Instruments Analytical Limited INCA Energy x-ray analysis system 3. A Si(Li) detector with approximately 133 eV resolution at 5.9 keV and an elevation angle of 35 degrees is used and records an x-ray energy spectrum as shown in FIG. 3.

The chemical formulae for all 63,000 entries in the Inorganic Crystal Structure Database (ICSD) (J. Res. Natl. Inst. Stand. Technol. 101, 217 (1996) is used as the dataset of candidate material compositions. Each chemical formula gives atomic proportions that are converted to mass percentage of elements in the material. A spectrum synthesis program (based on "Improved X-ray Spectrum Simulation for Electron Microprobe Analysis", Peter Duncumb, Ian R. Barkshire, Peter J. Statham, Microsc. Microanal. 7, 341-355, 2001.)) is used to synthesise the spectrum that would be detected for a material of this composition for a 20 kV incident beam, 35 degree elevation Si(Li) x-ray detector with 133 eV resolution, 70 degree sample tilt.

If $S_i$ is the count recorded in channel i for the measured spectrum and $R_i$ is the corresponding count in the reference spectrum, then a normalised cross correlation, NCC, value as a matching parameter, is calculated as $100.sum(S_i.R_i)/(sum(S_i^2).sum(R_i^2))^{0.5}$, where $sum(X_i)$ means the sum of variable $X_i$ over a range of channels i. In this example, a peak detection routine is used to find peaks in each spectrum and all channel counts that are not near to a peak are set to zero. NCC is then calculated for every candidate reference spectrum and a ranked list is generated as shown in Table 1:

TABLE 1

| Material | Match |
|---|---|
| 9237 Ga5 Gd3 O12 | 95.51 |
| 37145 Ga5 Gd3 O12 | 95.51 |
| 84874 Ga5 Gd3 O12 | 95.51 |
| 492 Ga1 Gd1 O3 | 92.94 |
| 65194 Ca0.95 Ga4 . . . | 92.58 |
| 202850 Ca0.95 Ga4 . . . | 92.58 |
| 85522 Ga3.32 Gd2 . . . | 90.01 |
| 90345 Ga1.272 Gd1 . . . | 88.54 |

Here we see that the best match is 95.51 for ICSD compound 9237 which has the identical formula to the measured sample. ICSD compounds 37145 and 84874 happen to have the same chemical formula and therefore the similarity measure is also 95.51. Compound 492 has the same chemical elements, Ga, Gd and O but in a different proportion; the synthesised spectrum from this compound therefore shows peaks in the same energy regions as the measured sample but with different relative intensity so the NCC value is slightly lower at 92.94. Other compounds produce different combinations of peaks and intensities and are lower down on the list of candidates.

EXAMPLE 2

Figure 4:
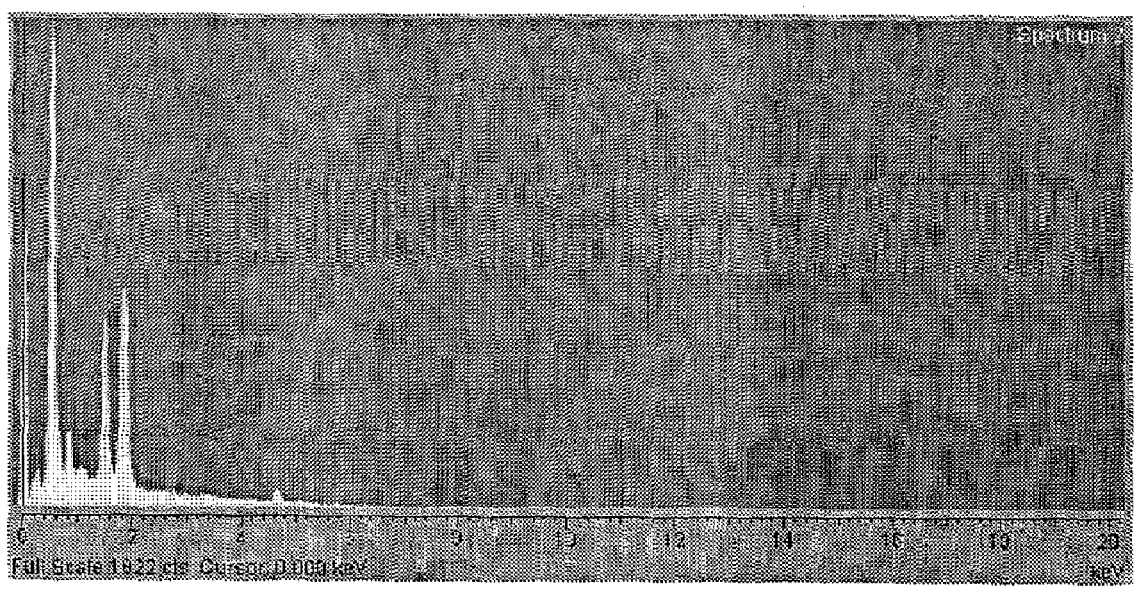
FIG. 4 is a spectrum according to a second example, showing charging of the specimen.

In the second example, a spectrum from a sample of $SrAlLaO_4$ is obtained using the same SEM 2 and acquisition conditions as for the first example. In this case, even though the incident electron beam energy is 20 keV the sample charges negatively under the electron beam so the DHL is reduced to about 6 keV as shown in FIG. 4.

Some elemental peaks such as SrKα 14.2 keV do not appear in the spectrum because the landing energy of electrons is below the critical excitation energy for these x-rays. Furthermore, the relative intensities for peaks that are excited are different than they would be if the sample were not charging. To find candidate materials that would show peaks in the spectrum at the same energy, irrespective of relative intensity, both measured and synthesised spectra are modified by replacing all channel counts in the vicinity of peaks by a suitable constant and channel counts elsewhere by 0. In this example, the peaks are detected by a "Top Hat" filter ("Deconvolution and background subtraction by least squares fitting with prefiltering of spectra", P J Statham, Anal. Chem. 49, 2149-2154, 1977) and the constant is set to +1 or −1 depending on the sign of the filtered result and whether the result exceeds the expected level for statistical fluctuations. In this case, the ranked list of NCC results for all candidates in the ICSD database are as shown in Table 2.

TABLE 2

| Material | Match |
|---|---|
| 41122 C12 H32 Al2 O28 | 71.22 |
| 35081 C1 Al2 O1 | 70.10 |
| 18204 C1 Al4 O4 | 68.62 |
| 69020 Al12 O19 Sr1 | 67.73 |
| 43155 Al12 O19 Sr1 | 67.73 |
| 2006 Al12 O19 Sr1 | 67.73 |

TABLE 2-continued

| Material | Match |
| --- | --- |
| 4116 Al2 La2 O7 Sr1 | 66.71 |
| 2817 Al4 O7 Sr1 | 64.53 |
| 34803 Al4 O7 Sr1 | 64.53 |
| 16751 Al4 O7 Sr1 | 64.53 |
| 72106 Al1 La1 O4 Sr1 | 64.23 |
| 54131 Al1 La1 O4 Sr1 | 64.23 |
| 91031 Al2 B2 O7 Sr1 | 64.05 |
| 89423 Al2 B2 O7 Sr1 | 64.05 |
| 26466 Al2 O4 Sr1 | 62.66 |
| 200671 Al12 O25 Sr7 | 62.65 |
| 200513 Al12 O25 Sr7 | 62.65 |
| 34086 Al12 O25 Sr7 | 62.65 |
| 32535 H4.5 Al18 O40.5 . . . | 62.65 |
| 61094 Al10.3333 Mg0.6 . . . | 62.49 |

Because the selection properties of the similarity measure (matching parameter) have been chosen to be insensitive to relative peak heights, a number of materials are ranked higher than the correct solution. However, the correct materials 72106 and 54131 have been retained in the top 20 candidates. If these 20 candidates are now compared to the measured sample using the matching parameter used for example 1, then the ranked list of Table 3 is obtained.

TABLE 3

| Material | Match |
| --- | --- |
| 41122 C12 H32 Al2 O28 | 83.63 |
| 89423 Al2 B2 O7 Sr1 | 78.11 |
| 91031 Al2 B2 O7 Sr1 | 78.11 |
| 54131 Al1 La1 O4 Sr1 | 71.09 |
| 72106 Al1 La1 O4 Sr1 | 71.09 |
| 32535 H4.5 Al18 O40.5 . . . | 69.17 |
| 4116 Al2 La2 O7 Sr1 | 68.19 |
| 34086 Al12 O25 Sr7 | 68.17 |

In this case, the materials with the correct composition (72106 and 54131) are now third in the ranking. When, in a further step, an electron backscattered diffraction pattern is measured from the sample, comparison of the crystallography against the top few candidates in the list confirms that 72106 is the most likely candidate material for the measured sample.

In this case where the sample is charging, the ranking of likely candidates is further improved by only calculating the NCC measure for channels below the DHL for the measured spectrum.

The examples above describe the operation of the invention. The ICSD database is just one example of a very large compilation of known materials. In different applications of the invention, the dataset can include one or more of existing compilations of known materials. Some examples could be: a set of standard steels or alloys, a set of standard glasses, a set of known contaminants for a semiconductor process, a set of minerals, a set of paints, a set of polymers.

Where the sample consists of a series of layers of different elements on a substrate, then it is sometimes possible to record x-ray spectra at one or more excitation conditions and from the characteristic peak intensities, deduce the thickness and composition of the layers ("Quantitative analysis of homogeneous or stratified microvolumes applying the model "PAP".", Pouchou, J. L. & Pichoir, F. (1991) In: Electron Probe Quantitation, Heinrich, K. F. J. & Newbury, D. E. (eds), Plenum Press, New York, 31-75). In general it is not possible to solve the structure and composition for a sample of arbitrarily complex structure using x-ray analysis. However, once a model for x-ray emission is established it is possible to use Monte Carlo analysis to synthesise a spectrum for any structure (e.g. R. Gauvin and E. Lifshin (2002), "On the Simulation of True EDS X-Ray Spectra", Microscopy & Microanalysis, Vol. 8, Supp. 2, pp. 430-431, 2002.) Thus, the database can include a set of materials data for complex reference samples that describe the geometric structure and material content of these samples. A spectrum synthesis model can then be used to calculate the spectrum for each of these references so that it can be compared to the measured spectrum from an unknown sample.

Example 2 shows how one matching parameter can be used to filter out a set of possible candidates from a large database and then another similarity measure is used to rank this subset. The first pass is made insensitive to known measurement problems (in example 2, this was potential charging of the specimen) and the top N candidates are assessed using a more specific similarity measure that would have been unsuitable to apply to the whole database for risk of eliminating the correct candidate from the top N.

In Examples 1 and 2, regions in the spectrum away from peaks are excluded in the NCC matching parameters. This is useful when the incident beam energy is high enough to excite characteristic lines from most elements yet the relative excitation of different lines may be uncertain, for example because of charging. However, low excitation energies may be preferable to reduce the volume of material being analysed (for example, to analyse small particles less than 100 nm in dimension in SEM, accelerating voltages less than 2 kV are required to keep x-ray excitation within the particle ). In this case, some elements in the material may not give rise to characteristic lines but all elements present influence the x-ray bremsstrahlung continuum. In the case where the sample is excited by x-rays, all elements present in the sample affect the inelastic (Compton) and elastic (Rayleigh) scattered radiation from the incident beam and thus influence the observed x-ray background. In such cases where the background in the spectrum carries useful information about material content, the NCC can be calculated for all channels in the spectrum rather than just the peaks.

Alternative mathematical formulae can be used to assess the closeness of the match. The relative contribution from different channels i can be weighted to make the similarity measure more or less sensitive to particular regions of the energy spectrum. This can be useful to de-emphasise regions that might exhibit artefact peaks or perhaps a common peak such as Si Ka emitted from a semiconductor substrate.

As mentioned with reference to Example 2, if the material is crystalline, then the electron backscatter diffraction pattern can be analysed to determine crystallographic parameters and these can be used to choose between the best matches. In the general case, any analytical technique can be used to distinguish between the top N selections for the current invention.

Where, despite the use of the method, it is difficult to distinguish between candidate materials/structure, the synthesised spectra of the materials can be shown on a visual display together with the spectrum from the unknown so that the user can choose the most appropriate compound using prior knowledge of the material.

If a further x-ray spectrum has been obtained under a substantially different condition (such as different microscope accelerating voltage or very different geometry), then x-ray spectra can be synthesised for the top few candidate compounds at this new condition and the unknown spectrum compared to find the best match.

A summary of the advantages deriving from the invention is now presented:
a) Spectra do not have to be measured on every candidate reference material or candidate structure so it is practical to have a large number of candidates in the reference database which forms the dataset;
b) Spectra do not have to be measured from reference materials under multiple conditions;
c) Spectra do not have to be measured from reference materials with the same x-ray detector that is to be used for the unknown because resolution and efficiency can be taken into account in the theoretical model.
d) Approaches based on analysis of spectral peaks, conversion to composition and comparison with a database of compositions may fail when there are spurious peaks in the spectrum because these produce false positive element identifications and may have a disproportionate effect on calculated composition because of the excitation characteristic. The new approach is only disturbed to an extent that the spurious peaks distort the spectrum and perturbs the similarity measure between spectra.
e) Approaches based on analysis of spectral peaks cannot in general determine the structure of inhomogeneous samples whereas the synthesis and best match approach can in principle find the best candidate structure in the dataset, irrespective of the complexity of the structure.
f) Approaches based on analysis of spectral peaks can only analyse material in conditions where characteristic lines are excited for all the elements of interest. However, the background and scattering from a sample is affected by all the elements present in the material, whether or not characteristic peaks are excited from those elements. Since the theoretical model can be used to synthesise the spectral peaks and the background radiation and any spectral features such as scatter peaks, it is possible to identify materials where characteristic lines are not available from all the elements present. This is particularly useful when low excitation voltages are used to analyse very small volumes of material.
g) The matching parameter can be chosen to make the method tolerant to likely measurement problems.

Appendix—Example Model

Description of Model

The ZAF theory of quantitative electron probe microanalysis has been well described in the literature (see, for example, Reed, 1993) and need not be repeated here, save to mention departures from convention. Note that for further details of the cited papers, the incorporated paper should be consulted. We follow the normal practice of calculating the peak intensity by integrating the ionization cross section Q for a given shell along the electron track, with allowance for the fraction (1−R) of the intensity lost by backscatter. This integration is most easily carried out as a function of electron energy E obtained from the stopping power relation $S = -dE/d(\Delta x)$, i.e., the rate of electron energy loss with mass thickness $\Delta x$. The intensity per unit solid angle $I_A$ arriving at the detector is then obtained by correcting for the fraction $f(\chi)$ which escapes from the sample and for the enhancement due to fluorescence excited by the primary radiation (1+F) and by the continuum (1+G). Thus, for an element A of mass fraction $C_A$, the intensity in a given line is $$I_A = (\omega_A \rho_A) \cdot R_A N_0 C_A / A_A \int Q_A / S_A \cdot dE \cdot f(\chi)_A \cdot (1+F) \cdot (1+G) \quad (2)$$

$$= \{Z\}\theta\{A\}\theta\{F\}$$

where $\omega A$ is the fluorescence yield for element A for the appropriate K, L, or $\rho$M shell, and pA is the proportion of the ensuing radiation that falls within the peak of interest. $A_A$ is the atomic weight of element A, and $N_0$ is Avogadro's number. Broadly, this equation divides into three parts associated with the generation of X-rays {Z}, their absorption {A}, and fluorescence {F}.

For the backscatter correction R, we use the expression of Duncumb and Reed (1967) and for stopping power S, that of Bethe (1930) with the modification proposed by Joy and Luo (1989). Absorption in the sample is corrected using a form of $f(\chi)$ proposed by Duncumb (1992), obtained by parameterization of a Monte Carlo calculation for the distribution in depth of the generated radiation. Characteristic fluorescence (1+F) is calculated from the procedures described by Reed (1993) and that from the continuum (1+G) is simplified from Pouchou (1994). While all of these choices are capable of improvement, they are easily separable, fast to compute, and give results that are well within target accuracy.

This leaves the ionization cross section Q, for which the absolute values for each of the K, L, or M shells is left open for adjustment. The variation of Q with electron energy E is well described by a modification of the Bethe cross section used by Green and Cosslett (1961) of the form $$Q = q_{K,L,M} \cdot m \cdot (\ln U)/(E_c^2 \cdot U^m) \quad (3)$$

where Ec is the critical excitation potential for the analyzed peak and U is the overvoltage ratio E/Ec. m is a constant for each shell in the range 0.7-0.9, adjusted to fit the shape of the relationship to experiment; a similar approach has been used by Pouchou (1994), who found m to be a slowly varying function of atomic number. Direct measurements by Llovet (2000a) for the L and M shells and by Llovet (2000b) for the K shell also accord generally with this form. Finally, the multipliers qK, qL, and qM are set by experiment to match the observed intensities from each shell to one another and to those results for which the intensities are known in absolute terms.

Where the intensity from a characteristic line in the sample is measured as a ratio to that from a pure standard—the original k-ratio method—the value of the q multiplier cancels out, as does the fluorescence yield TA and peak fraction pA. In addition, the correction for continuum fluorescence is usually found to be negligible. The accuracy of the remaining ZAF theory, of which many variants exist, has been tested by analyzing the composition of a large number of known alloys by their K, L, or Mα emission, using pure standards. The results are expressed as a histogram of the ratio of the measured to the true composition, having a certain mean ratio and standard deviation about the mean. Many authors have used this process to illustrate the accuracy of their particular approaches and these have been well summarized by Heinrich (1992).

The combination of procedures described above comes close to the best available. In an analysis of 756 known samples, for example, Duncumb (1992) found that the method used here, named "PhiZAF" gave a mean error of <0.1% with a standard deviation of 2.4%. Thus the ZAF correction procedure itself is not likely to limit the accuracy of spectrum simulation; there are much greater uncertainties to be found in equation (2) in the values to be adopted for the fluorescence yield T, the relative height p, and the ionization cross section constants qK,L,M. What matters for any given peak is the product of all three, but for this to be calculable for each line in each shell for all atomic numbers, the physical distinction between them must be preserved as far as possible.

However, we note the concept introduced by Joy (1998) of the "X-ray generation cross section," combining the fluorescence yield v with the ionization cross section Q, and agree that this may provide a convenient simplification, though it does conceal the fact that two different processes are involved.

The fluorescence yield values cannot be entirely decoupled from the relative line intensities. Equation (2) is most easily studied in terms of the alpha peaks, but some ambiguity exists as to the correct values of $\omega_A$ to be associated with each value of $T_A$. Schreiber and Wims (1982a) define this factor as the proportion of the total radiation falling into the combined $\alpha 1$, $\alpha 2$ peaks and have derived values of $P_A$ as a function of atomic number for each of the K, L, and M series. However, for the present purpose we wish to synthesize the $\alpha 1$ and $\alpha 2$ lines separately, so that the progressive separation that occurs with increasing atomic number can be realistically modeled. Also, we wish to synthesize all the other lines in the series, and the most practical way of doing this is to use tables that express the line height as a proportion of the $\alpha 1$ line, taken as unity.

At the present state of knowledge, tables of relative intensity are incomplete or inconsistent, especially at low energies, though a second article by Schreiber and Wims (1982b) provides useful data for some of the higher-energy lines. We have chosen to use the set from Oxford Instruments Inca software, evolved experimentally from the tables of Johnson and White (1970). The line ratios within each shell or sub-shell have been normalized to add up to unity, in order to distribute the total intensity from a given ionization unchanged. This means that the intensity calculated for a given line is dependent on all the others and any adjustment of the relative intensity tables must be made iteratively. However, within the accuracy we are attempting this is not difficult.

For simplicity, we assume that the resulting tables are independent of beam energy, and that the excitation energies of the L and M shells are those of the $L_{III}$ or $M_V$ edges, respectively. We do, however, correct subsequently for the different absorption that a line may suffer in comparison with the alpha line—i.e., the tables are assumed to give the intensity generated and not that emitted from the sample. As a result of the normalization, the effect of Coster-Kronig transitions, which redistribute vacancies within the L and M shells, is largely expressed in the relative intensity tables, leaving the fluorescence yields as relatively smoothly varying functions of atomic number.

We base our fluorescence yields for the K and L shells on the well-established tables of Krause (1979), which summarize and supplement the earlier review by Bambynek et al. (1972). Below atomic number 10 for the K shell and 50 for the $L_{III}$ shell, the estimated uncertainty reported by Krause exceeds 10%. Likewise, for the M shell, Oz et al. (1999) report an increasing spread in published values as Z falls below 72 (Hf), exceeding a factor of 2 at 57 (La). In creating our own set of yield tables from the results described below, we therefore aim to be consistent with the reported values for the higher atomic numbers, but can allow some significant divergence for the lighter elements without going outside the bounds of physical credibility. We thus finish with a set of "effective fluorescent yields" closely agreeing with published values at higher energies and fitted to our own data at the lower energies. Below 1 keV, chemical effects may dominate, increasing the spread on figures obtained from compounds.

With the freedom to set the $q_{K,L,M}$ multipliers in Equation (2), we can then bring the average intensities for the alpha lines in each shell into consistency with one another and with such measurements that we know are absolute—i.e., for which the detector geometry and incident current are accurately known. Other lines in a given series are then scaled from the appropriate $P_A$ values, correcting for any effects of differential absorption.

Thus the principle has been to accept the existing tables for relative heights, expecting that they will require modification in the future, and to determine empirically an "effective" fluorescence yield, based on established values at the higher energies. Any overall differences between the K, L, and M shell intensities is then taken up in the multiplier $q_{K,L,M}$ for the ionization cross section, and these again should be close to those reported in the literature.

With a large number of spectra available, it was possible to extract the background continuum for a variety of conditions of incident energy and mean atomic number of the target. As a development of Kramers' law, we found that the shape and intensity in the generated spectrum could be independently adjusted by an expression of the form $$I_V = k \cdot Z \cdot F(Z,E_0) \cdot (U-1)^{P(Z)} \qquad (4)$$

The exponent P (in the range 0.9-1.15) controls the shape of the spectrum—that is, the distribution of intensity between high and low energies—whereas the factor F (0.7-1.2) governs the intensity overall. Surprisingly, P seems to be a function only of Z whereas F clearly depends on both Z and $E_0$. Both represent significant departures from unity.

Comparisons of the measured spectrum with the synthesized background (in white), for carbon, silicon, copper, and gold, at 20 kV—all obtained with a detector having an atmospheric thin window—exposes the spectral detail at low energies but the detector must be well characterized in this region, as noted below. Also important are corrections for absorption and backscatter, which must be made at each point in the background. To speed the computation, these are made by simplified methods akin to those described by Statham (1976) and do not appear to be critical to the final result. It is a further benefit of a fast model that it is easy to test the sensitivity of the end result to changes in various input parameters, such as detector window thickness, and hence to determine those that must be accurately known.

With the ability to calculate the continuum to within a few percent, it is easy to calculate the total background intensity. This is generally of the same order of intensity as the major peaks, and so may be found with a much better statistical accuracy than the background in a narrow channel near the peak. The ratio of peak intensity/total background intensity, hereafter called the PB-ratio, is useful in at least two respects:

1. It enables the synthesized spectrum to be directly compared with a measured spectrum obtained from a detector for which the solid angle is unknown, since the PB-ratio is independent of solid angle (and indeed of probe current and counting time). We have used the PB-ratio to great advantage in developing the simulation model, enabling us to make use of the spectra from six or eight different instruments for which the solid angle was not available. It is still, of course, necessary to know how the detector efficiency varies with energy, since the detector curve materially affects the shape of the continuum.
2. Knowing the PB-ratio helps in the identification of overlapping peaks, where possible alternatives may be distinguishable by their different PB-ratios. Statham (2000) has shown how the PB-ratio from the composite $CrL\alpha$ (573 eV) and $CrL1$ (500 eV) peak from pure chromium is considerably smaller than that from $Cr_2O_3$, because of the oxygen K peak at 520 eV. The distinction is not obvious from the peak shape but is clear from the PB-ratio. Thus an accurate knowledge of PB-ratio gives compositional information, which is additional to the peak position and intensity—information that in principle permits an absolute analysis to be carried out without the use of standards.

For model validation purposes, data were gathered from three different sources, using different detectors and take-off angles. From 309 spectra there were 167 Kα, 145 Lα, and 48 Mα peaks, as shown in Table 2, totaling 360 alpha peaks in all. These ranged in energy from 0.28 keV to 14.1 keV and approximately half of the peaks in each series fell below 2 keV in energy, which is the region we particularly wanted to test. About 80% of the spectra were taken under the most commonly used conditions of 10-20 kV, with the remainder serving to test the extremes of 5 and 30 kV. There were 98 spectra from compound samples, and 86 peaks of these were below 2 keV. No attempt was made at this stage to test the simulation accuracy for other than alpha peaks, representing 360 independent measurements. Thus the results were sensitive to inaccuracies in the relative height tables only insofar as these determine the proportion of radiation falling within the alpha peak.

The samples were coated with carbon after polishing, normally to a thickness of 10-15 nm. The simulation allowed for the presence of a carbon layer, correcting for the retardation of the incident beam, the characteristic peak generated within the layer, and the absorption of X-rays emerging from the sample beneath. If the sample itself were carbon-free, the thickness could be accurately determined from the height of the measured peak at 0.28 keV, but it was usually sufficient to assume a thickness of 15 nm.

The detector resolution was simulated by the normal method of adding in quadrature the contribution from electronic noise to that produced by the finite number of electron-hole pairs released in the silicon. By matching synthesized and measured peaks at the high- and low-energy end of a given spectrum it was possible to calibrate a detector within 1-2 eV (full width at half maximum height), and the detectors used showed resolutions from 130 to 140 eV (at the energy of MnKα). In fact, an accurate knowledge of resolution was only necessary where a peak under investigation was partially overlapped by another, as, for example, $MoL\alpha_1$ by $MoL\beta_1$. In other cases, the simulation integrated the peak intensity between ±3 standard deviations either side of the maximum, assumed to be Gaussian.

Window efficiency was more of a problem, particularly as it affected the spectrum near the window cut-off at low energies. With the beryllium window this occurred below about 2 keV, whereas for the thin-film windows it was well below 1 keV. The Super atmospheric thin window (SATW) and Super ultra-thin window (SUTW) consist of a polymer film supported on a silicon grid, for which nominal values of the thickness and dimensions are available. There is also an aluminium film of known thickness. It is thus possible to calculate the transmission at all wavelengths, and to test the sensitivity to errors in these assumptions by running the results for slightly different thicknesses. After some iteration a consistent picture emerges and, in fact, the manufacturers' figures appeared to be accurate enough for the present purpose. In the case of the beryllium window (Be) this was not the case, and a nominal thickness of 8 μm appeared to be more nearly 10.5 μm.

A further uncertainty in the case of the SATW and SUTW windows is the obscuration by the supporting grid, which effectively reduces the solid angle subtended by the detector. Fortunately this is not a problem in the method adopted in this work, since the reduction affects the peak and the background equally. For energies above 10 keV the grid becomes transmitting, and this effect is allowed for in our model. Absolute calibration was carried out with the Be detector, restricted by an aperture of known diameter and distance from the sample.

The construction of the detector itself is not critical in determining efficiency. Assumptions have to be made about the conducting layer, the dead layer (if any), and the thickness of the silicon, and the final results may again be tested for sensitivity to any error in these assumptions. Within the 10% accuracy we are targeting we do not believe that the uncertainties in the detector efficiency need be a limiting factor.

The spectra were processed in four batches, containing the Kα peaks, Lα peaks, Mα peaks, and all 360 peaks together. The last category afforded a check on the former three and was split into two parts, corresponding to peak energies above and below 2 keV. The following operations were performed on each spectrum:

Filter out peaks and create interpolated background

Synthesize spectrum from known composition

Scale synthesized background to interpolated spectrum

Subtract synthesized background to obtain measured peaks

Select each peak in turn and calculate the peak intensity/total background

Compare the PB-ratio for the measured and synthesized peaks and record ratio.

When each batch is complete, the mean and standard deviation of the error ratios are calculated as a measure of the accuracy of simulation. The average error ratio for each element in each shell is then used to calculate a notional fluorescence yield that would bring this ratio to unity. The resulting curves for K, L, and M yields against atomic number are matched to the data of Krause and Oz, as noted above, and used to create smoothed curves of the effective yields at low energies. All this is part of an iterative process, from which the final results are given in the cited paper.

It is implied in the above process that we have correctly set the multipliers $q_K$, $q_L$, and qM in equation (3) which determine the intensities of emission from each of the three shells. In addition, the overall intensity of the continuum background is governed by the factor k in equation (4). Although the calculation of PB-ratio depends only on the ratio q/k, we need to know the absolute value of each in order to estimate the total count rate and hence the statistical noise. Fortunately, this is usually not required with high accuracy.

Because of the difficulty of comparing different forms of expression in the literature, we have determined our own value of $q_k$ using the grid-free Be window detector, for which the solid angle subtended at the sample is known to within a few percent. We used a dataset of 167 K lines, selecting 14 peaks with energies >3 keV, where the Be window transmission is close to unity. The standard deviation of this restricted set is only 2.8%, so that the error in $q_K$ should be well below 10%. Knowing $q_K$, we can then derive the background factor k from the mean value of the PB-ratios taken across all the K lines; then, knowing k, we can find $q_L$ and $q_M$ from the corresponding L and M datasets. These values are then checked on each of the K, L, and M sets and finally on the combined set of 360 samples.

As a check of the accuracy of $q_K$, we use it to calculate the efficiency of X-ray production under known conditions and compare this with published work of the efficiency for CuKα radiation at an overvoltage ratio of 2, i.e., with an electron beam of 18 kV. This condition is probably the best known in the literature. The present work falls at the bottom end of the range of 6.4-7.6 quoted by Lifshin et al. (1977) but agrees closely with that of Green and Cosslett (1968) and of Joy (1998). We conclude that the absolute intensity is probably accurate to within a few percent, which is quite adequate for the assessment of noise statistics.

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

What is claimed is:

1. A method of identifying a material using an x-ray emission characteristic, the method comprising:
   a) obtaining x-ray data representing a monitored x-ray emission characteristic of a specimen in response to an incident energy beam;
   b) obtaining a pre-existing dataset comprising composition data of a plurality of materials and wherein the material of the specimen is contained within the dataset;
   c) calculating predicted x-ray data for each of the material in the dataset using the composition data and a spectrum simulation model;
   d) comparing the obtained and the predicted x-ray data using a calculated matching parameter and using said calculated matching parameter to rank said materials in said dataset; and
   e) determining the identities of a plurality of materials, based upon the comparison ranking, wherein one material from said plurality of materials is likely to be the material of the specimen.

2. A method according to claim 1, wherein the predicted x-ray data represents the x-ray data which would be obtained if the incident energy beam were incident upon a specimen containing the corresponding material.

3. A method according to claim 1, wherein the x-ray emission characteristic is an x-ray spectrum.

4. A method according to claim 1, wherein in the calculating step (c) the said composition data and data describing the analytical conditions under which the data in step (a) are obtained, are each used as inputs into the spectrum simulation model.

5. A method according to claim 1, wherein the calculating step (c) is further based upon data describing the detector response function of the x-ray apparatus used in obtaining the data of step (a).

6. A method according to claim 1, wherein the calculating step (c) further includes a calculation of the influence upon the x-ray emission characteristic of the specimen becoming electrically charged.

7. A method according to claim 1, wherein, when the x-ray characteristic is an x-ray spectrum, the matching parameter in step (d) is calculated only in regions within the spectrum containing peaks and is independent of the peak intensity in such regions.

8. A method according to claim 1, wherein, when the x-ray characteristic is an x-ray spectrum, the matching parameter in step (d) is calculated based upon the bremsstrahlung background of the spectrum.

9. A method according to claim 1, wherein, when the x-ray characteristic is an x-ray spectrum and the obtained x-ray data comprises multichannel detector data, the matching parameter in step (d) is calculated based upon the normalised cross correlation coefficient for all channels of the obtained x-ray data.

10. A method according to claim 9, wherein the matching parameter in step (d) is calculated based upon only the channels near peaks in the spectrum which are significant compared to statistical noise.

11. A method according to claim 9, wherein the matching parameter in step (d) is calculated based upon a weighting factor for different channels.

12. A method according to claim 1, wherein the matching parameter in step (d) is calculated based upon a weighted sum or product of the matching parameters.

13. A method according to claim 1, wherein a first matching parameter is used to select the top N likely materials from the dataset, and a second matching parameter is used to further ran the selected N materials.

14. A method according to claim 1, wherein the obtained data within the dataset further comprises structure data and wherein the identified material includes an associated structure of the specimen.

15. A method according to claim 14, wherein the obtained data comprises the dimensions of one or more components of the associated structure.

16. A method according to claim 1, wherein the obtained data for each associated material to be identified, comprises a corresponding identifying code.

17. A method according to claim 1, wherein the x-ray characteristic data in step (a) represents data obtained from the specimen under two or more different incident beam conditions, wherein the predicted data in step (c) are calculated for each different condition, and wherein the determination in step (e) is based upon the different incident beam conditions.

18. A method according to claim 17, wherein the different conditions comprise different incident beam energies.

19. A method according to claim 1, wherein, prior to step (a) the method further comprises the steps of:
   i) positioning the specimen within an x-ray emission detecting apparatus comprising an x-ray detector;
   ii) causing the energy beam in be incident upon the specimen so as to cause the specimen to emit x-rays; and,
   iii) detecting the x-rays with the detector.

20. A method according to claim 1, wherein the incident beam at least one of an electron beam, x-ray beam, or ion beam.

21. A method according to claim 1, wherein the model calculates x-ray intensities based upon an x-ray generation contribution, an absorption contribution and a fluorescence contribution.

22. A method according to claim 21, wherein the model calculates the x-ray background continuum.

23. A method according to claim 22, wherein the model calculates the ratio of peak intensity to total background intensity.

24. A method according to claim 1, wherein the model is a Monte Carlo model.

25. A method according to claim 1 further comprising, prior to step (a), validating the accuracy of the calculation method for step (c) by comparing test calculations with experimentally obtained test x-ray data.

26. A method according to claim 25, wherein the calculations are calibrated using the test data.

27. A computer program comprising computer program code means adapted to perform the method of claim 1 when said computer program is executed upon a computer.

28. A computer readable medium comprising a computer program according to claim 27.

29. An x-ray system for material identification comprising:
- an x-ray analysis apparatus in which is placed in use a specimen containing a material to be identified, the apparatus having a beam generation device, a specimen holder and an x-ray detector; and,
- a controller adapted in use to perform the method according to claim 1.

30. A system according to claim 29, wherein the apparatus comprises an electron microscope or an x-ray fluorescence analysis instrument.

31. A system according to claim 29, wherein an x-ray beam is collimated or focused by an x-ray optic to a small region.

32. A system according to claim 29, wherein the detector is a solid state detector or a gaseous proportional detector.

* * * * *